US010357212B2

(12) United States Patent
Lindenberg et al.

(10) Patent No.: US 10,357,212 B2
(45) Date of Patent: Jul. 23, 2019

(54) METHOD FOR CAPTURING A THREE-DIMENSIONAL X-RAY IMAGE

(71) Applicant: Sirona Dental Systems GmbH, Bensheim (DE)

(72) Inventors: Kai Lindenberg, Wersau (DE); Stefan Wundrak, Gronau (DE)

(73) Assignee: Sirona Dental Systems GMBH, Bensheim (DE)

( * ) Notice: Subject to any disclaimer, the term of this patent is extended or adjusted under 35 U.S.C. 154(b) by 177 days.

(21) Appl. No.: 14/905,750

(22) PCT Filed: Jul. 16, 2014

(86) PCT No.: PCT/EP2014/065217
§ 371 (c)(1),
(2) Date: Jan. 15, 2016

(87) PCT Pub. No.: WO2015/007765
PCT Pub. Date: Jan. 22, 2015

(65) Prior Publication Data
US 2016/0157796 A1 Jun. 9, 2016

(30) Foreign Application Priority Data
Jul. 16, 2013 (DE) .................. 10 2013 213 876

(51) Int. Cl.
A61B 6/00 (2006.01)
A61B 6/03 (2006.01)
(Continued)

(52) U.S. Cl.
CPC ............... *A61B 6/06* (2013.01); *A61B 6/032* (2013.01); *A61B 6/14* (2013.01); *A61B 6/405* (2013.01);
(Continued)

(58) Field of Classification Search
CPC .. A61B 6/032; A61B 6/06; A61B 6/14; A61B 6/405; A61B 6/4266; A61B 6/4435;
(Continued)

(56) References Cited

U.S. PATENT DOCUMENTS 6,061,426 A 5/2000 Linders et al.
6,181,774 B1 1/2001 Prins et al.
(Continued)

FOREIGN PATENT DOCUMENTS

DE 102 21 634 A1 12/2003
DE 699 10 524 T2 6/2004
(Continued)

OTHER PUBLICATIONS

International Search Report dated Oct. 21, 2014, International Application No. PCT/EP2014/065217.
(Continued)

Primary Examiner — Chih-Cheng Kao
(74) Attorney, Agent, or Firm — Venable LLP

(57) ABSTRACT

The invention relates to a method for capturing a three-dimensional x-ray image (1) of an object (2) by means of an x-ray system (3) comprising an x-ray source (4), an x-ray detector (5) and a shutter matrix (7), the shutter matrix (7) having a plurality of shutter elements (18), the x-ray absorption properties of which are controllable. In the first method step, at least one region (21) to be captured of the object (2) is defined, wherein settings are planned for the individual shutter elements (18) of the shutter matrix (7) for different rotary positions (14, 15, 16, 17), taking into account the defined area (21) to be captured. Then, a plurality of two-dimensional x-ray images is captured from the planned rotary positions (14, 15, 16, 17) during at least one partial rotation (9) using the planned settings of the shutter elements (18), wherein the overall three-dimensional x-ray image (1) of the area (21) to be captured is generated from the individual two-dimensional x-ray images.

23 Claims, 2 Drawing Sheets

(51) Int. Cl.
*A61B 6/06* (2006.01)
*A61B 6/14* (2006.01)
*G21K 1/04* (2006.01)
*A61F 13/20* (2006.01)

(52) U.S. Cl.
CPC .......... *A61B 6/4266* (2013.01); *A61B 6/4435* (2013.01); *A61B 6/469* (2013.01); *A61B 6/488* (2013.01); *A61B 6/5217* (2013.01); *A61B 6/542* (2013.01); *A61F 13/20* (2013.01); *G21K 1/046* (2013.01); *A61B 6/463* (2013.01); *A61B 6/466* (2013.01)

(58) Field of Classification Search
CPC ......... A61B 6/463; A61B 6/466; A61B 6/469; A61B 6/488; A61B 6/5217; A61B 6/542; G21K 1/046
See application file for complete search history.

(56) References Cited

U.S. PATENT DOCUMENTS

| | | |
|---|---|---|
| 8,644,448 B2 | 2/2014 | Klingenbeck |
| 2005/0089138 A1* | 4/2005 | Toth .................. A61B 6/032 378/20 |
| 2005/0117707 A1* | 6/2005 | Baier .................. A61B 6/032 378/156 |
| 2007/0092058 A1* | 4/2007 | Mattson .................. A61B 6/032 378/15 |
| 2009/0168966 A1* | 7/2009 | Suzuki .................. A61B 6/032 378/116 |
| 2013/0162645 A1 | 6/2013 | Ulrici |

FOREIGN PATENT DOCUMENTS

| | | |
|---|---|---|
| DE | 11 2006 002 694 T5 | 9/2008 |
| DE | 10 2010 040 812 A1 | 3/2012 |
| JP | 2000-023970 A | 1/2000 |
| JP | 2002-517007 A | 6/2002 |
| JP | 2006-311882 A | 11/2006 |
| JP | 4567064 B2 | 10/2010 |
| JP | 2010-284325 A | 12/2010 |

OTHER PUBLICATIONS

Written Opinion of International Search Authority, International Application No. PCT/EP2014/065217, dated Oct. 21, 2014.
International Preliminary Report on Patentability dated Jan. 19, 2016, International Application No. PCT/EP2014/065217.
Office Action in German Patent Appln No. 10 2013 213 876.8 dated Feb. 6, 2014.
Mar. 6, 2018 Office Action in Japanese Patent Application No. 2016-526595 (with English translation).

* cited by examiner

METHOD FOR CAPTURING A THREE-DIMENSIONAL X-RAY IMAGE

TECHNICAL FIELD

The invention relates to a method for capturing an x-ray image of an object by means of an x-ray system comprising an x-ray source, an x-ray detector and a shutter matrix, the shutter matrix having a plurality of shutter elements, the x-ray absorption properties of which are controllable.

PRIOR ART

Several x-ray systems that use a shutter matrix having a plurality of shutter elements are known from the prior art.

DE 699 10 524 T2 discloses an x-ray testing device comprising an x-ray filter made up of a plurality of filter elements, the capacity of which to absorb x-rays can be adjusted by changing the amount of x-ray absorbing fluid within individual filter elements. The adhesion of the x-ray absorbing fluid to the inside wall of capillary tubes of such elements is a function of the electrical voltage that is applied to the capillary tubes.

X-ray systems having fixed shutter arrangements for defining an area to be captured are known from the prior art. Such shutter systems can usually only set rectangular capture areas.

A disadvantage of such systems is therefore the fact that a rectangular capture area is defined around the actual target object, and the tissue of the patient surrounding the target object is unnecessarily exposed to radiation, such that the dose load is increased.

Therefore, the object of the present invention is to provide a method for capturing an x-ray image that allows for a three-dimensional x-ray capture with the lowest possible dose.

DESCRIPTION OF THE INVENTION

The invention relates to a method for capturing a three-dimensional x-ray image of an object by means of an x-ray system comprising an x-ray source, an x-ray detector and a shutter matrix. The shutter matrix has a plurality of shutter elements, the x-ray absorption properties of which can be controlled. In one step of the method, at least one area of the object to be captured is defined. In another step of the method, settings are planned for the individual shutter elements of the shutter matrix for different rotary positions, taking into account the defined area to be captured. Then, multiple two-dimensional x-ray images from the planned rotary positions are captured using the planned settings of the shutter elements during at least one partial rotation. The overall three-dimensional x-ray image of the area to be captured is then generated from the individual two-dimensional x-ray images.

The three-dimensional x-ray image can, for example, be a DVT x-ray image or a CT x-ray image. In what is known as the digital volume tomography (DVT) method or in what is known as the computer tomography (CT) method, the x-ray source and the x-ray detector are moved within a defined plane around the object to be captured (such as the head of a patient), wherein two-dimensional x-ray images are generated from different directions, wherein a three-dimensional volume is calculated from these projected images in the next step.

This calculated three-dimensional x-ray image can then be displayed in user software by means of a display device, such as a screen. Therefore, imaging is based on the continuous capture of the projection from different directions, wherein the three-dimensional x-ray image is calculated using a reconstruction method, wherein the respective x-ray absorption values are assigned to what are known as the voxels of the three-dimensional x-ray image.

The shutter matrix can, for example, comprise shutter elements that function according to the electrocapillary principle, wherein the shutter matrix is a bundle with a very large number of capillary tubes that each have a connection to an x-ray absorbing fluid at one end, wherein the adhesion of the x-ray absorbing fluid to the inside wall of such a capillary tube is a function of the electric voltage that is applied to the corresponding capillary tube. Thus, the individual capillary tubes can be controlled with regard to their x-ray absorption capacity. The shutter matrix can, for example, comprise a 100×100 matrix arrangement with dimensions of 5 cm×5 cm. An even higher resolution, for example in a 200×200 matrix arrangement, makes a higher resolution of the shutter matrix possible.

The area to be captured can, for example, be the entire maxilla, the entire mandible, the left mandibular joint and/or the right mandibular joint. However, the defined area to be captured can also include only a group of individual teeth.

The settings of the shutter matrix for the individual rotary positions are therefore calculated using a computer, such that, for example, x-rays from the x-ray source that must be projected onto the surrounding areas outside of the defined area to be captured are completely masked by means of the corresponding shutter elements, wherein only the x-rays that are projected onto the area to be captured are passed through. Therefore, the settings of the shutter elements comprise the absorption values to be set for the individual shutter elements for each of the rotary positions.

For a partial rotation of, for example, 180°, the two-dimensional x-ray images can be captured from the rotary positions in increments of 1°, i.e., for 180 different rotary positions. A smaller rotation of, for example, 90° or a larger rotation with 270° in 0.5° increments is possible, wherein a higher number of two-dimensional x-ray images results in fewer artifacts and thus a better image quality of the reconstructed three-dimensional x-ray image. However, this is also associated with a higher dose load if the dose for a single image stays the same.

An advantage of this method is that, in comparison to conventional methods, only the area to be captured is exposed to x-rays, thereby minimizing the dose load. The tissue surrounding the area to be captured is thereby not exposed to radiation.

Another advantage of the present method is that multiple, non-contiguous areas can be detected with a minimum dose. In contrast, given conventional methods, areas that were separated from each other would have needed to be measured successively in multiple images.

Another advantage is that, if capturing what is known as a sub-volume, a gantry mechanism of a conventional x-ray device can be produced in a significantly simplified manner because the center of volume is displaced via the shutter matrix, and not via the actuators that are arranged on the gantry.

The area to be captured can advantageously be defined in an overview image captured before the image.

The overview image of the object already exists and was captured before the inventive method was carried out.

The area to be captured can therefore be defined in a computer-assisted manner via a display device such as a monitor, either manually or automatically in this overview image.

The overview image can advantageously be a two-dimensional optical image, a three-dimensional optical image, a three-dimensional x-ray image or a two-dimensional x-ray image.

Therefore, the overview image can be, for example, a three-dimensional optical image, such as a DVT image or a CT image; a conventional two-dimensional x-ray image; or also a three-dimensional optical image, wherein the three-dimensional optical image can be captured, for example, by means of a dental camera that is based on a stripe projection method.

The overview image can also be, for example, a single optical image or video recording that includes the object to be captured and was taken by means of a conventional video camera or a stereo video camera.

The area to be captured can advantageously be manually defined in an overview image by a user by means of a computer, using input means.

As a result, the user can select the appertaining area to be captured in the overview image in a computer-assisted manner via the display device (such as a monitor) using input means (such as a keyboard or a mouse).

The area to be captured can advantageously be defined in the overview image automatically by means of a computer, wherein certain predefined anatomical areas are recognized using a computer-assisted search algorithm.

The computer-assisted search algorithm used can be a conventional pattern recognition algorithm and/or a segmentation algorithm.

In known search algorithms, objects are segmented and searched for matching structures. A pattern recognition procedure can, for example, include subsequent steps, namely preprocessing, the acquisition of the features, the reduction of the features and the classification of the features. During processing, unwanted or irrelevant components of the image data are removed. In the acquisition of features, certain features are obtained from the image data by comparing the images to known models from a database, such as a database of characteristic teeth or jawbones. The automatic comparison is done using transformation functions and scaling, a comparison factor being determined by calculating a variance between a model made from the image data and an expanded model made from the database. When the features are reduced, a check is made to determine which features are relevant to the division of classes and which can be omitted. In particular, the samples of the teeth and jaw bone obtained are relevant to this method, wherein the obtained features can pass unnoticed. In the last step of classification, the essential recognized features, such as teeth and characteristic forms of the jawbone, are divided into related classes, such as incisors, molars, tooth roots and jawbones. In the acquisition of features, known methods such as grid analysis, cluster analysis and pattern matching can be used.

The area to be captured can advantageously be defined in a preliminary selection, wherein—using known positional relations of the x-ray source, of the x-ray detector and of the shutter matrix relative to each other, and using dimensions of a model of a patient stored in a data memory—a certain anatomical structure of the patient's head is defined in an additional step as the area to be captured.

As a result, no previous overview image is necessary because a model head stored in the database is used to define the area to be captured. In this process, for example, a maxilla or a mandible of the model head can be selected that corresponds to the shape of the maxilla or mandible to be captured as accurately as possible.

The area to be captured can advantageously include at least one anatomical structure.

As a result, the area to be captured includes at least one anatomical structure, such as a maxilla, a mandible or a group of teeth.

The anatomical structure can advantageously be a maxilla, a mandible, a right mandibular joint and/or a left mandibular joint, or a partial structure of these.

As a result, only the respective anatomical structure to be captured is selected.

The settings for the shutter elements of the shutter matrix can advantageously be adjusted to an anatomical structure to be captured during the rotation, wherein the anatomical structure to be captured (for example the mandible) is detected in at least one previous two-dimensional x-ray image from a previous rotary position, and the settings of the shutter elements for a subsequent x-ray image from a subsequent rotary position are then adapted to the dimensions of the detected anatomical structure from the previous x-ray image of the previous rotary position.

The settings of the shutter elements are therefore calculated for each rotary position as a function of the two-dimensional x-ray image of the previous rotary position. The settings for the individual shutter elements for the new rotary position can be calculated using a reconstruction process. The known positional relation between the x-ray source, the x-ray detector, the shutter matrix and the defined area to be captured are thus used to calculate which shutter elements in the new rotary position should mask out x-rays or allow them to pass through.

A segmentation process for detecting the defined anatomical structure in the x-ray image of the previous rotary position can also be used when the settings of the shutter elements are calculated for the new rotary position. As a result, the selected anatomical structure is therefore searched for at each rotary position during rotation, and the shutter elements are set accordingly. This has the advantage that, if the anatomical structure in a two-dimensional x-ray image was selected as an overview image, and therefore the dimensions of the selected anatomical structure are only known from one direction, the selected anatomical structure is determined step by step in the captured two-dimensional x-ray images for each rotary position during rotation, and the shutter matrix is adjusted accordingly. Slight movements of the object (such as the head of a patient) relative to the x-ray system can also be compensated for during rotation. The advantage is therefore that the dimensions of the anatomical structure to be captured, such as the maxilla or the mandible, do not need to be completely known and are determined step by step for each rotary position only during imaging.

The settings for the shutter elements of the shutter matrix can advantageously be adjusted to the anatomical structure step by step, image by image, for each rotary position.

As a result, the settings of the shutter matrix are adjusted step by step for each rotary position.

The shutter matrix can advantageously be an arrangement of shutter elements arranged in one plane.

Therefore, the shutter matrix can, for example, have a shutter arrangement of 100×100 shutter elements.

The shutter matrix can advantageously be a linear arrangement of shutter elements arranged in one row.

The shutter matrix can, for example, have a linear arrangement of 100 shutter elements.

A further second area to be captured, which is spatially separated from the first area to be captured, can advantageously be defined in addition to said first area to be captured, wherein the shutter elements of the shutter matrix are controlled in such a way that the first area to be captured and the second area to be captured are captured simultaneously.

As a result, two or more spatially separated areas to be captured or volumes to be captured can be captured simultaneously in a three-dimensional x-ray image. The shutter matrix is controlled in such a way that only beams that cross the defined areas or volumes reach the object. The remaining x-rays are masked out such that the entire dose of the x-ray image is reduced, in comparison to conventional methods in which every area must be measured individually.

BRIEF DESCRIPTION OF THE DRAWINGS

The invention is explained with reference to the drawings. In the drawings.

EXEMPLARY EMBODIMENT

Figure 1:
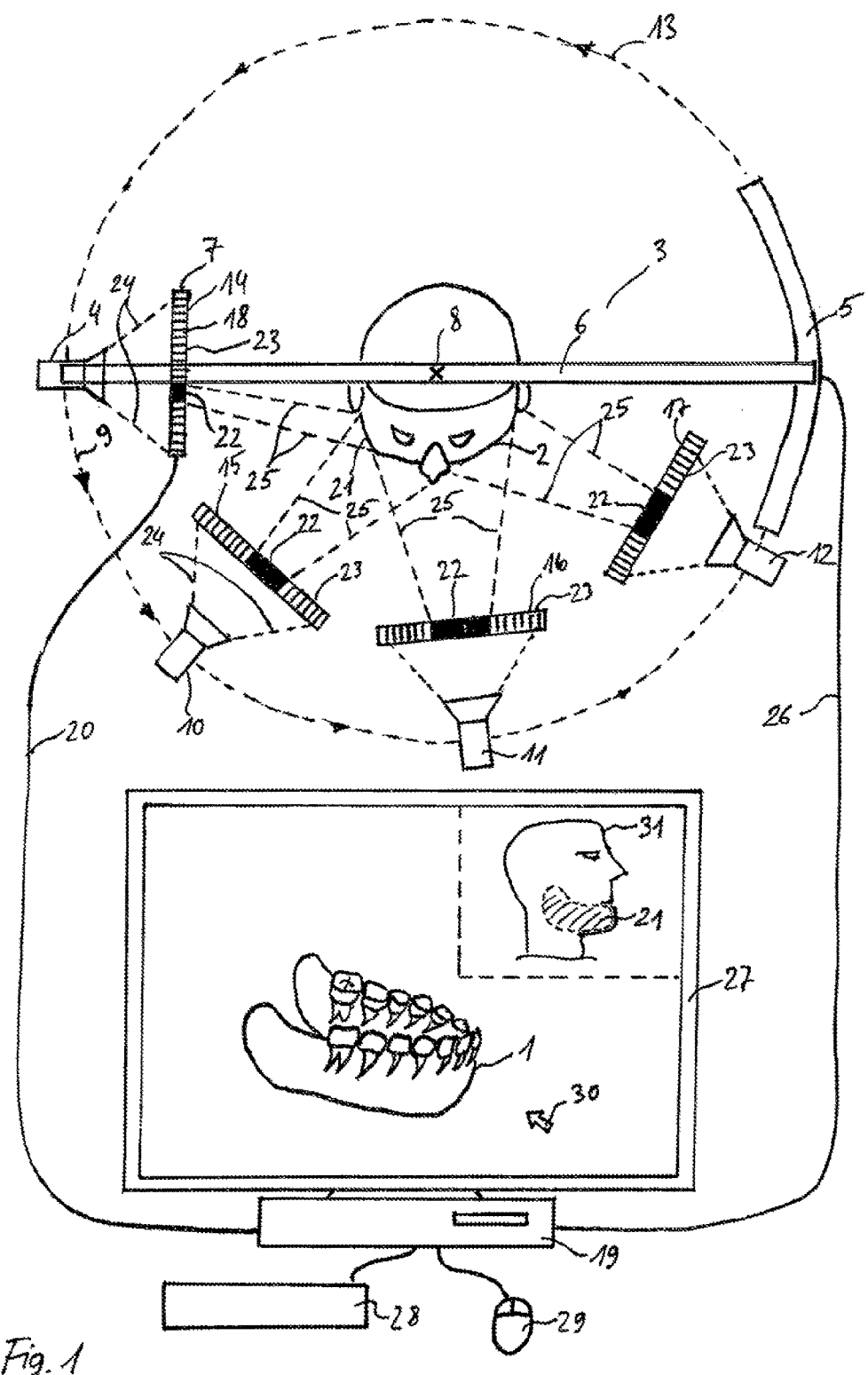
FIG. 1 shows a sketch for clarifying the method for capturing a three-dimensional x-ray image.

FIG. 1 shows a sketch to clarify the method for capturing a three-dimensional x-ray image 1 of an object 2, such as a patient's head, by means of an x-ray system 3 comprising an x-ray source 4, a rectangular x-ray detector 5, a support arm 6 and a shutter matrix 7. The x-ray source 4 and the x-ray detector 5 are arranged at the opposite ends of the support arm 6, which is borne in the x-ray system 3 in such a way that the support arm 6 is rotated about a common axis of rotation 8 (which is shown as a cross) along with the x-ray source 4, the x-ray detector 5 and the shutter matrix 7 attached to the support arm 6. During an at least partial rotation, the x-ray source 4 is moved along a first circular trajectory 9 to a second rotary position 10, to a third rotary position 11 and then to a fourth rotary position 12. Accordingly, the x-ray detector 5 is rotated along a second trajectory 13. Starting from a first rotary position 14, the shutter matrix 7 is thus likewise moved together with the support arm 6 to a second rotary position 15, to a third rotary position 16 and then to a fourth rotary position 17.

The shutter matrix 7 has a plurality of shutter elements 18, the x-ray absorption properties of which can be controlled. The control occurs by means of a computer 19, which sends the control data to the shutter matrix 7 via a cable connection 20. The data can also be transferred wirelessly between the data matrix 7 and the computer 19. The shutter elements 18 of the shutter matrix 7 can be, for example, capillary tubes that are filled with an x-ray absorbing fluid, wherein the adhesion of the x-ray absorbing fluid to the inside wall of the capillary tubes is a function of the electrical voltage that is applied to the corresponding capillary tubes. In the first step of the method, an area 21 to be captured (which is depicted with a dashed line and corresponds to a mandible in this case) is selected from an overview image 31 or alternatively from a model head from a database. The overview image 22 can be, for example, a two-dimensional x-ray image, a three-dimensional optical image or a three-dimensional x-ray image of the patient that was captured before the method was performed. Then, settings for the individual shutter elements 18 of the shutter matrix 7 are calculated by means of the computer 19 for the first rotary position 14, taking into account the defined area 21 to be captured (namely the mandible). The shutter elements 18 of a first shutter matrix area 22, which is marked in black, are controlled in such a way that they have the lowest x-ray absorption rate possible, the remaining shutter elements 18 within a second shutter matrix area 23 outside of the first shutter matrix area 22 being controlled in such a way that the x-ray absorption rate is as high as possible. Thus, the x-rays 24 emitted by the x-ray source 4 within the second shutter matrix area 23 are masked out, and those within the first shutter matrix area 22 are passed through to the object 2. As a result, only the defined area 21 to be captured—namely the mandible in the case shown—is exposed to the transmitted x-rays 25. The x-ray data of a first two-dimensional x-ray image captured by means of the x-ray detector 5 are then sent to the computer 19 either by means of a cable connection 26 or, alternatively, wirelessly. The first two-dimensional x-ray image, which was captured from the first rotary position 14, can then be searched for the area 21 to be defined (namely the mandible) using computer-assisted search algorithms. The dimensions or contours of the mandible 21 from the first two-dimensional x-ray image are then used to calculate the settings of the x-ray matrix 7 for the second rotary position 15. Then, the x-ray source 4 is moved into the second rotary position 15 together with the x-ray matrix 7. The shutter elements 18 of the shutter matrix 7 are then controlled in such a way that the first shutter matrix area 22 allows x-rays to pass through and the second shutter matrix area 23 masks out x-rays, such that only the capture x-rays 25 pass through to the object 2. The x-ray detector 5 then captures a second two-dimensional x-ray image in the second rotary position 15 and sends the x-ray data to the computer 19. The mandible 21 is detected in it again using the search algorithms. Then, the settings of the shutter matrix 7 are calculated for the third rotary position 16. The third two-dimensional x-ray image is also captured in the same way from the third rotary position 16, and the fourth two-dimensional x-ray image is captured in the same way from the fourth rotary position 17. In the last step of the method, the complete three-dimensional x-ray image 1 of the mandible 21, which is displayed via a monitor 27, is generated from the individual two-dimensional x-ray images of the rotary positions 14, 15, 16 and 17 via reconstruction. Choosing the area 21 to be captured in the overview image 22, as well as navigating in the three-dimensional x-ray image 1, can be done manually by the user using input means, such as a keyboard 28 and a mouse 29, via a cursor 30. Therefore, according to this method the three-dimensional x-ray image 1 of the area 21 to be captured (namely the mandible) is generated, wherein the surrounding tissue of the mandible is not exposed to radiation, thereby minimizing the dose load of the patient.

Figure 2:
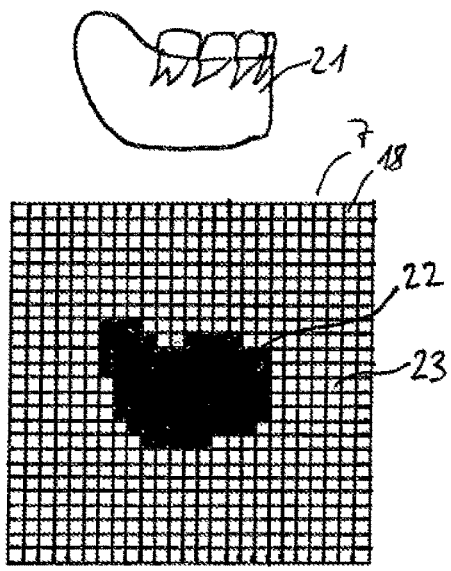
FIG. 2 shows a sketch of the shutter matrix with the shutter elements in a first rotary position.

FIG. 2 shows a sketch of the shutter matrix 7 with shutter elements 18, wherein the shutter arrangement depicts a rectangular arrangement of 25×25 shutter elements. A shutter arrangement of 100×100 or even more shutter elements can also be used, and has the advantage of a higher resolution of the shutter matrix 7.

The area 21 to be captured, namely the mandible, is shown from the perspective of the first rotary position 14 from FIG. 1. The shutter matrix 7 was controlled in such a way that the shutter elements 18 within the first shutter matrix area 22 (marked in black) allow x-rays to pass through and the remaining shutter elements 18 within the second shutter matrix area 23 mask out the x-rays.

Figure 3:
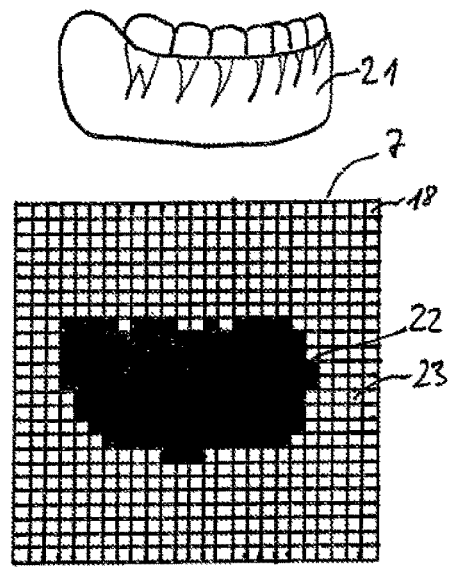
FIG. 3 shows a sketch of the shutter matrix with the shutter elements in a second rotary position.
Figure 4:
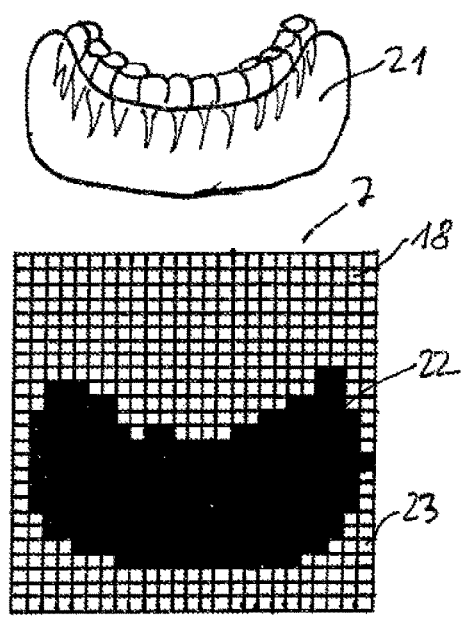
FIG. 4 shows a sketch of the shutter matrix with the shutter elements in a third rotary position.
Figure 5:
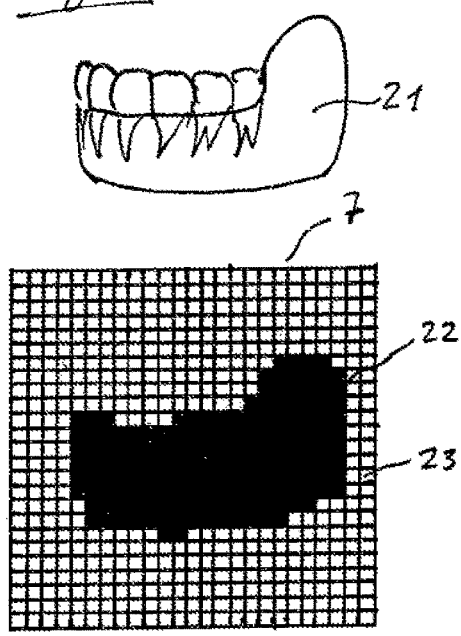
FIG. 5 shows a sketch of the shutter matrix with the shutter elements in a fourth rotary position.

FIG. 3 shows the mandible 21 and the shutter matrix 7 in the second rotary position 15; FIG. 4 shows them in the third rotary position 16; and FIG. 5 shows them in the fourth rotary position 17. A sketch is thus used to clarify the manner in which the shutter matrix is controlled during the rotation around the object 2. Therefore, the two-dimensional x-ray images are captured and the adjustments of the shutter matrix 7 are made for a multitude of rotary positions 14, 15, 16 and 17, the rotary position being adjustable in increments of, for example, 1° to 5°. For a three-dimensional x-ray image, a partial rotation is sufficient, for example between 60° and 180°.

REFERENCE LIST 1 x-ray image
2 object
3 x-ray system
4 x-ray source
5 x-ray detector
6 support arm
7 shutter matrix
8 common axis of rotation
9 first trajectory
10 second rotary position of the x-ray source
11 third rotary position of the x-ray source
12 fourth rotary position of the x-ray source
13 second trajectory
14 first rotary position of the shutter matrix
15 second rotary position of the shutter matrix
16 third rotary position of the shutter matrix
17 fourth rotary position of the shutter matrix
18 shutter elements
19 computer
20 cable connection
21 area to be captured
22 first shutter matrix area
23 second shutter matrix area
24 x-rays
25 capture x-rays
26 cable connection
27 monitor
28 keyboard
29 mouse
30 cursor
31 overview image

The invention claimed is:

1. A method for generating a three-dimensional x-ray image of an object using an x-ray system that includes: an x-ray source, an x-ray detector, a data processing system, and a shutter matrix that includes a plurality of shutter elements with controllable x-ray absorption properties, with the x-ray source configured to transmit x-rays to the shutter matrix, and with the x-ray source being rotatable relative to object, the method comprising:
  calculating settings for the shutter elements of the shutter matrix based on an area of the object to be captured, the settings corresponding to different rotary positions of the x-ray source relative to the object,
  wherein the settings for the shutter elements define a first shutter matrix area with shutter elements that substantially transmit x-rays and a second shutter matrix area with shutter elements that substantially attenuate x-rays, and
  wherein the first shutter matrix area corresponds to a cross-section of the area of the object to be captured at each of the rotary positions of the x-ray source relative to the object;
  capturing two-dimensional x-ray images respectively corresponding to the rotary positions during at least one partial rotation of the x-ray source relative to the object, the x-ray detector, and the shutter matrix using the settings for the shutter elements; and
  generating a three-dimensional x-ray image of the area to be captured from the two-dimensional x-ray images,
  wherein the settings for all of the rotary positions of the x-ray source throughout the at least one partial rotation are calculated before the two-dimensional x-ray images are captured.

2. A method according to claim 1, wherein the area of the object to be captured is defined based on an overview image captured before the two-dimensional x-ray images are captured.

3. A method according to claim 2, wherein the overview image is one of: a two-dimensional optical image, a three-dimensional optical image, a two-dimensional x-ray image, or a three-dimensional x-ray image.

4. A method according to claim 2, further comprising:
  receiving a user selection of the area of the object to be captured based on the overview image from an input device.

5. A method according to claim 2, wherein the area of the object to be captured is defined based on predefined anatomical areas recognized by a computer-assisted search algorithm analyzing the overview image.

6. A method according to claim 1, wherein the area of the object to be captured is defined as an anatomical structure of a model head using (i) known positional relations of the x-ray source, the x-ray detector, and the shutter matrix relative to each other, and (ii) dimensions of a model of a patient stored in a data memory.

7. A method according to claim 1, wherein the area of the object to be captured comprises at least one anatomical structure.

8. A method according to claim 7, wherein the at least one anatomical structure is at least one of a maxilla, a mandible, a right mandibular joint, or a left mandibular joint.

9. A method according to claim 1, further comprising:
  adjusting a setting for the shutter elements that corresponds to a later rotary position of the x-ray source based on a two-dimensional x-ray image from an earlier rotary position of the x-ray source.

10. A method according to claim 1, further comprising:
  adjusting the settings for the shutter elements respectively corresponding to the rotary positions of the x-ray source except for a setting for the shutter elements corresponding to an initial rotary position of the x-ray source,
  wherein an adjustment of a setting for the shutter elements for a rotary position of the x-ray source is based on a two-dimensional x-ray image captured from an earlier rotary position of the x-ray source.

11. A method according to claim 1, wherein the shutter matrix is an arrangement of the shutter elements within one plane.

12. A method according to claim 1, wherein the shutter matrix is a line-shaped arrangement of the shutter elements arranged in a single row.

13. A method according to claim 1, wherein the settings for the plurality of shutter elements are calculated, in the calculating, to allow for the first shutter matrix area to include a second area of the object to be captured, the second area being spatially separated from the area to be captured.

14. A method for capturing x-ray images of an object using an x-ray system that includes: an x-ray source, an x-ray detector, a data processing system, and a shutter matrix that includes shutter elements with controllable x-ray absorption properties, wherein the x-ray source transmits x-rays to the shutter matrix, and wherein the x-ray source, the x-ray detector, and the shutter matrix are configured to rotate through a plurality of rotary positions relative to the object, the method comprising:

calculating an initial setting for the shutter elements to define a first shutter matrix area for the initial rotary position of the x-ray source based on an area of the object to be captured, wherein the first shutter matrix area includes shutter elements that substantially transmit x-rays and corresponds to a cross-section of the area of the object to be captured at the initial rotary position of the x-ray source;

capturing a two-dimensional x-ray image corresponding to the initial rotary position of the x-ray source relative to the object using the initial setting for the shutter elements;

for each of a plurality of rotary positions of the x-ray source about the object, except the initial rotary position of the x-ray source:
    (i) calculating a setting for the shutter elements based on (i-i) a two-dimensional x-ray image captured at a preceding rotary position of the x-ray source and (i-ii) a positional relationship between the x-ray source, the x-ray detector, the shutter matrix, and an area of the object to be captured,
      wherein the setting for the shutter elements defines the first shutter matrix area for the rotary position of the x-ray source and corresponds to a cross-section of the area of the object to be captured at the rotary position of the x-ray source, and
    (ii) capturing a two-dimensional x-ray image based on the setting for the shutter elements; and generating a three-dimensional x-ray image from (1) the two-dimensional x-ray image corresponding to the initial rotary position of the x-ray source and (2) the two-dimensional x-ray images corresponding to the plurality of rotary positions of the x-ray source about the object, except the initial rotary position of the x-ray source.

15. A method according to claim 14, wherein the area of the object to be captured is defined based on an overview image captured before the two-dimensional x-ray image corresponding to the initial rotary position is captured,
  wherein the overview image is one of: a two-dimensional optical image, a three-dimensional optical image, a two-dimensional x-ray image, or a three-dimensional x-ray image.

16. A method according to claim 15, wherein the area of the object to be captured is defined based on predefined anatomical areas recognized by a computer-assisted search algorithm analyzing the overview image.

17. A method according to claim 14, wherein the area of the object to be captured is defined as an anatomical structure of a model head using (i) known positional relations of the x-ray source, the x-ray detector, and the shutter matrix relative to each other, and (ii) dimensions of a model of a patient stored in a data memory.

18. A method according to claim 14, wherein the area of the object to be captured comprises at least one anatomical structure.

19. A method according to claim 18, wherein the at least one anatomical structure is at least one of a maxilla, a mandible, a right mandibular joint, or a left mandibular joint.

20. A method according to claim 14, wherein the shutter matrix is an arrangement of the shutter elements within one plane.

21. A method according to claim 14, wherein the shutter matrix is a line-shaped arrangement of the shutter elements arranged in a single row.

22. A method according to claim 14, wherein the initial setting for the shutter elements and the settings for the shutter elements for the plurality of rotary positions of the x-ray source, except the initial rotary position of the x-ray source, allow for the first shutter matrix area to include a second area of the object to be captured, the second area being spatially separated from the area to be captured.

23. An x-ray imaging system comprising:
  an x-ray source;
  an x-ray detector;
  a shutter matrix that includes shutter elements with controllable x-ray absorption properties, wherein the x-ray source transmits x-rays to the shutter matrix, and wherein the x-ray source, the x-ray detector, and the shutter matrix are configured to rotate through a plurality of rotary positions relative to the object; and
  a computer configured to:
    calculate an initial setting for the shutter elements to define a first shutter matrix area for an initial rotary position of the x-ray source based on an area of an object to be captured, wherein the first shutter matrix area includes shutter elements that substantially transmit x-rays and corresponds to a cross-section of the area of the object to be captured at the initial rotary position of the x-ray source,
    capture a two-dimensional x-ray image corresponding to the initial rotary position of the x-ray source using the initial setting for the shutter elements,
    for each of the plurality of rotary positions of the x-ray source, except the initial rotary position of the x-ray source:
      (i) calculating a setting for the shutter elements based on (i-i) a two-dimensional x-ray image captured at a preceding rotary position of the x-ray source and (i-ii) a positional relationship between the x-ray source, the x-ray detector, the shutter matrix, and an area of the object to be captured,
        wherein the setting for the shutter elements defines the first shutter matrix area for the rotary position of the x-ray source and corresponds to a cross-section of the area of the object to be captured at the rotary position of the x-ray source, and
      (ii) capture a two-dimensional x-ray image based on the setting for the shutter elements and the area of the object to be captured, and
    generate a three-dimensional x-ray image from (1) the two-dimensional x-ray image corresponding to the initial rotary position of the x-ray source and (2) the two-dimensional x-ray images corresponding to the plurality of rotary positions of the x-ray source about the object, except the initial rotary position of the x-ray source.

* * * * *